(12) United States Patent
Takimoto

(10) Patent No.: US 7,758,506 B2
(45) Date of Patent: Jul. 20, 2010

(54) ULTRASOUND DIAGNOSIS APPARATUS

(75) Inventor: Masao Takimoto, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 989 days.

(21) Appl. No.: 11/006,658

(22) Filed: Dec. 8, 2004

(65) Prior Publication Data

US 2005/0203401 A1    Sep. 15, 2005

(30) Foreign Application Priority Data

Dec. 8, 2003    (JP)    ............................. 2003-409238

(51) Int. Cl.
  *A61B 8/00*    (2006.01)
(52) U.S. Cl. ..................... 600/441; 600/437; 600/453
(58) Field of Classification Search ................. 600/437, 600/441, 453
  See application file for complete search history.

(56) References Cited

U.S. PATENT DOCUMENTS 6,508,766 B2 *   1/2003   Sato et al. ................... 600/441

FOREIGN PATENT DOCUMENTS

| JP | 3-186254 | 8/1991 |
|---|---|---|
| JP | 2001-149370 | 6/2001 |
| JP | 2001149370 A * | 6/2001 |

* cited by examiner

*Primary Examiner*—Brian Casler
*Assistant Examiner*—John F Ramirez
(74) *Attorney, Agent, or Firm*—Oblon, Spivak, McClelland, Maier & Neustadt, L.L.P.

(57) ABSTRACT

An ultrasound diagnosis apparatus includes a scanner, an input unit, a change unit, a prediction unit, a processor, and a second processor. The scanner is configured to conduct an ultrasound segment scan by alternating a B-mode scan and a Doppler-mode scan. The input unit is configured to input an instruction. The change unit is configured to change a first period of the B-mode scan and a second period of the Doppler-mode scan in accordance with the instruction. The prediction unit is configured to predict a first Doppler signal with respect to the first period. The processor is configured to prepare an Doppler-mode image based on the first Doppler signal and a second Doppler signal resulting from the Doppler-mode scan. The second processor is configured to prepare a B-mode image based on a B-mode signal resulting from the B-mode scan.

16 Claims, 7 Drawing Sheets

ULTRASOUND DIAGNOSIS APPARATUS

CROSS-REFERENCE TO RELATED APPLICATION

This application is based upon and claims the benefit of priority from prior Japanese Patent Application No. P2003-409238, filed on Dec. 8, 2003, the entire contents of which are incorporated herein by reference.

BACKGROUND OF THE INVENTION

1. Field of the Invention

The present invention relates to an ultrasound diagnosis apparatus which prepares B-mode images and Doppler-mode images. The present invention also relates to a method of preparing B-mode images and Doppler-mode images.

2. Discussion of the Background

In an ultrasound diagnosis apparatus, it is known to often display both Doppler-mode images (or Doppler spectrums) and B-mode images (or tomograms) of a specimen such as, for example, a patient substantially in real time. To accomplish such a display, two techniques shown in FIGS. 1A and 1B are known as its examples. FIG. 1A is an illustration for explaining one of the techniques which may be called an interleaving a scan. FIG. 1B is an illustration for explaining the other one of the techniques which may be called a segment scan. In FIGS. 1A and 1B, 'B' represents a B-mode scan or a B-color-mode scan (hereinafter referred to as a B-mode scan), and 'D' represents a Doppler-mode scan.

As shown in FIG. 1A, one Doppler-mode scan is conducted every after three B-mode scans. Since the Doppler-mode scan is regularly repeated at a constant interval, its sampling frequency cannot be made higher than an actual rate frequency. In addition, artifacts may often appear in the Doppler-mode images and the B-mode images because of echo signals remaining mutually between in the Doppler-mode and the B-mode.

As shown in FIG. 1B, a non-Doppler segment period and a Doppler segment period are alternately repeated. In the non-Doppler segment period, the B-mode scans are conducted a plurality of times. In the Doppler segment period, the Doppler scans are conducted a plurality of times. Accordingly, it may be possible to avoid the problems occurring in the interleaving scan. However, Doppler signals resulting from the Doppler scans are not available for the non-Doppler segment periods, and accordingly, it is necessary to conduct interpolation processing of Doppler signals with respect to the non-Doppler segment periods. In the interpolation processing, a missing signal estimation (MSE) technique may often be used. According to the U.S. Pat. No. 4,559,953, for example, it may be at most about ten milliseconds (10 ms) when the living body is construed to be in a steady condition. Therefore, a period of about ten milliseconds may be a maximum predictable period in the interpolation processing.

In the ultrasound diagnosis apparatus, linear predictive coefficients are calculated based on steady signals in the body of the specimen so as to determine an auto-regressive model (AR model). Accordingly, linearly predicted signals as the AR model are generated with Gaussian noise as a resource of the linearly predicted signals in order to interpolate missing signals with respect to the non-Doppler segment period The difference between the predicted signals and unobtained actual Doppler signals is construed as an error. When the body of the specimen is in a steady condition, the error is small while the error becomes large when the body is in an unsteady condition. The large error leads to vertically-striped Doppler-mode (or spectrum) images resulting from an unsmooth connection between one segment and the next segment.

Such problematic images may noticeably be produced particularly in the small number of AR parameters, for example, when there is small number of samples (or scans) in the Doppler segment period and/or when a frame rate is low. This problem may be avoided by increasing the frame rate and/or the number of samples (or scans) in the Doppler segment period. This increase, however, causes another problem. It is not possible to decrease a range of Doppler velocity. In addition, since each interval between one non-Doppler segment period and the next, that is, between B-mode scans in one non-Doppler segment period and the next, becomes too long, a stripe due to a time phase difference between the one non-Doppler segment period and the next appears in a B-mode image, particularly when the B-mode image is a B-color-mode image. Accordingly, the B-mode image quality noticeably becomes deteriorated.

To solve this problem, it is known to decrease the prediction error of Doppler signals with specimen's body signals correlating to the Doppler signals as described in, for example, paragraphs [0019] to [0038] of Japanese Patent Application Publication No. 2001-149370.

As described above, an image quality of a B-mode image (or B-mode image quality), an image quality of a Doppler-mode image (or Doppler-mode image quality) and a frame rate may be determined by setting the Doppler segment period and the non-Doppler segment period. The B-mode image quality, the Doppler-mode image quality, and the frame rate are mutually correlated. Accordingly, the Doppler segment period and the non-Doppler segment period are preferably not determined uniquely or fixed, but may be expected to be freely changed according to a diagnosis part, an image display style, a user's preference, and/or the like.

SUMMARY OF THE INVENTION

According to the first aspect of the present invention, there is provided an ultrasound diagnosis apparatus including a scanner, an input unit, a change unit, a prediction unit, a processor, and a second processor. The scanner is configured to conduct an ultrasound segment scan by alternating a B-mode scan and a Doppler-mode scan, The input unit is configured to input an instruction. The change unit is configured to change a first period of the B-mode scan and a second period of the Doppler-mode scan in accordance with the instruction. The prediction unit is configured to predict a first Doppler signal with respect to the first period. The processor is configured to prepare a Doppler-mode image based on the first Doppler signal and a second Doppler signal resulting from the Doppler-mode scan. The second processor is configured to prepare a B-mode image based on a B-mode signal resulting from the B-mode scan.

According to the second aspect of the present invention, there is provided an ultrasound diagnosis apparatus including a scanner, an input unit, and a change unit. The scanner is configured to conduct an ultrasound segment scan by alternating a B-mode scan and a Doppler-mode scan. The input unit is configured to input an instruction. The change unit is configured to change a first period of the B-mode scan and a second period of the Doppler-mode scan in accordance with the instruction. The change unit is further configured to change at least one of a scan-line density, a sampling number, an upper limit of a pulse repetition frequency, and a number of echo signals to receive in parallel, with respect to the B-mode scan. The echo signals results from ultrasound signals generated in the first period in accordance with the instruction.

According to the third aspect of the present invention, there is provided a method of preparing a B-mode image and a Doppler-mode image. The method begins by inputting an instruction and changing a first period of a B-mode scan and a second period of a Doppler-mode scan in accordance with the instruction. The method continues by conducting an ultrasound segment scan by alternating the B-mode scan and the Doppler-mode scan and predicting a first Doppler signal with respect to the first period. The method still continues by preparing the Doppler-mode image based on the first Doppler signal and a second Doppler signal resulting from the Doppler-mode scan and also preparing the B-mode image based on a B-mode signal resulting from the B-mode scan.

According to the third aspect of the present invention, there is provided a computer readable medium on which is stored a program module for preparing a B-mode image and a Doppler-mode image. The program module has instructions, which when executed perform steps including receiving an instruction and changing a first period of a B-mode scan and a second period of a Doppler-mode scan in accordance with the instruction. The steps continue by conducting an ultrasound segment scan by alternating the B-mode scan and the Doppler-mode scan and predicting a first Doppler signal with respect to the first period. The steps further continue by preparing the Doppler-mode image based on the first Doppler signal and a second Doppler signal resulting from the Doppler-mode scan and preparing the B-mode image based on a B-mode signal resulting from the B-mode scan.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DESCRIPTION OF THE PREFERRED EMBODIMENTS

Embodiments of the present invention will be described with reference to the accompanying drawings.

Figures 1A, 1B:
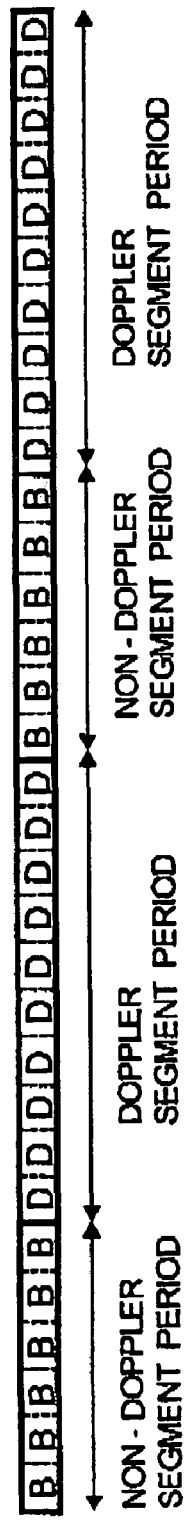
FIG. 1A is an illustration for explaining an interleaving scan technique.
FIG. 1B is an illustration for explaining a segment scan technique.
Figure 2:
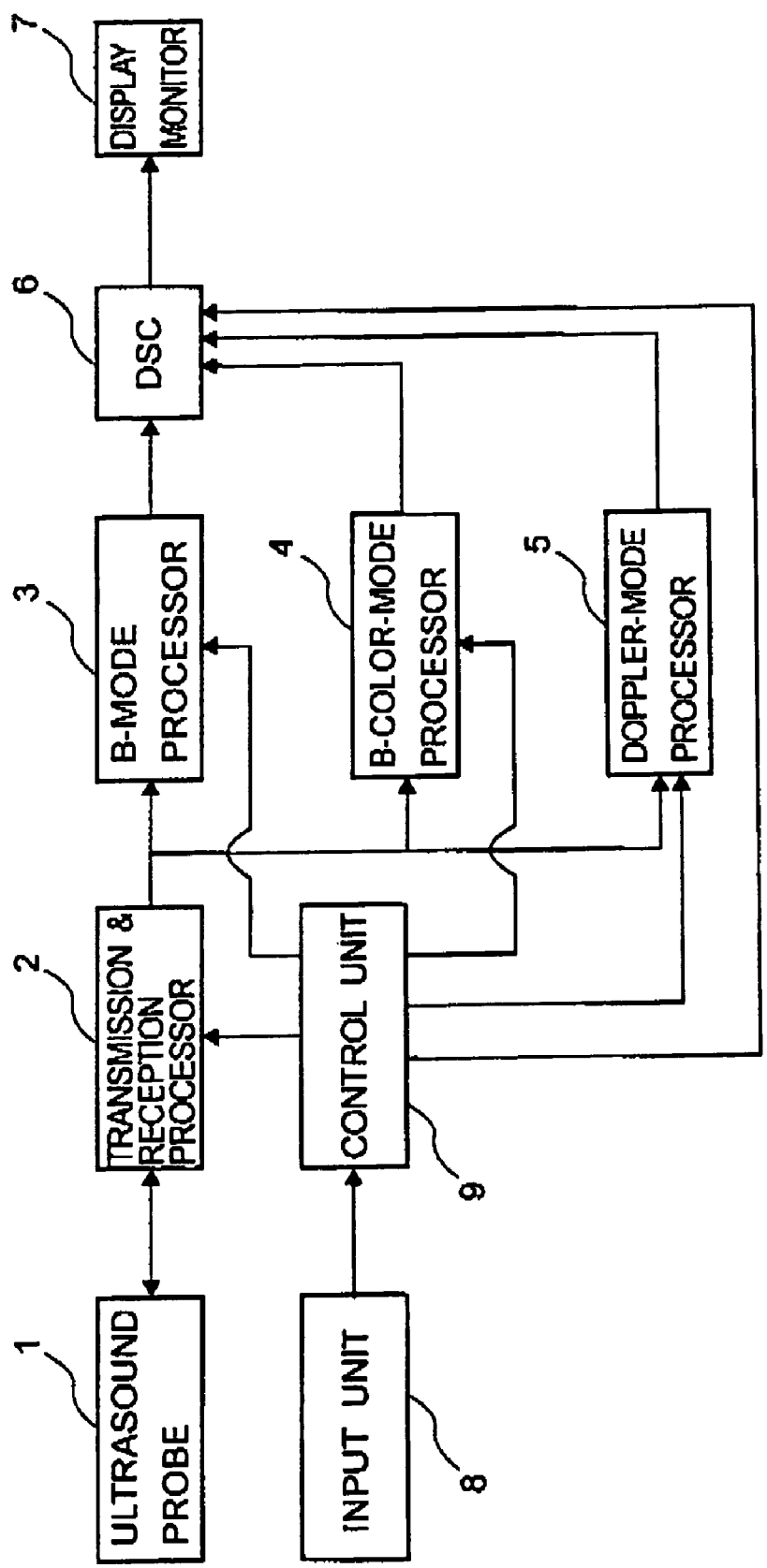
FIG. 2 is a block diagram showing an exemplary configuration of an ultrasound diagnosis apparatus.

FIG. 2 is a block diagram showing an exemplary configuration of an ultrasound diagnosis apparatus. As shown in FIG. 2, the ultrasound diagnosis apparatus includes an ultrasound probe 1, a transmission and reception processor 2, a B-mode processor 3, a B-color-mode processor 4, a Doppler-mode processor 5, a digital scan converter (DSC) 6, a display monitor 7, an input unit 8, and a control unit 9.

The ultrasound probe 1 transmits ultrasound signals (waves, or pulses) to the specimen and receives echo signals from the specimen as 'a scanner'. The echo signals result from the transmitted ultrasound signals which are reflected inside the body of the specimen. In other words, the ultrasound probe 1 electronically scans by transmitting the ultrasound signals towards a target area inside the specimen's body while the ultrasound probe 1 receives the echo signals from inside the specimen's body. The ultrasound probe 1 conducts at least the segment scan by alternating the B-mode scans in the non-Doppler segment period and the Doppler-mode scans in the Doppler segment period. In the non-Doppler segment period, ultrasound transmission is repeated by transmitting a predetermined number of ultrasound beams (or by conducting a predetermined number of scans) in the corresponding number of directions so as to scan a predetermined range of the target area. Accordingly, the B-mode scans in one non-Doppler segment period results in a part of a B-mode image. When the B-mode scans are conducted in different ranges of the target area in two or more non-Doppler segment periods, a plurality part of the B-mode image are obtained. The plurality part of the B-mode image are combined and provided as one B-mode mage. In the Doppler segment period, ultrasound transmission is repeated by transmitting a predetermined number of ultrasound beams in a predetermined direction so as to obtain various information including velocity information, dispersion information, and power information. The non-Doppler segment period may correspond to 'the first period' while the Doppler segment period may correspond to 'the second period'.

The transmission and reception processor 2 provides the ultrasound probe 1 with electrical signals so that the ultrasound probe 1 transmits the ultrasound signals. The transmission and reception processor 2 also receives the echo signals from the ultrasound probe 1.

The B-mode processor 3 receives the echo signals from the transmission and reception processor 2, and prepares B-mode image data based on the received echo signals substantially in real time for a user of the ultrasound diagnosis apparatus. For example, the B-mode processor 3 conducts delayed addition processing and analog-to digital (A/D) conversion processing on the received echo signals so as to prepare the B-mode image data. The B-color-mode processor 4 may conduct a frequency analysis processing in a similar manner to the B-mode processor 3, and prepares B-color-mode image data substantially in real time for the user. The B-mode processor 3 and/or the B-color-mode processor 4 may correspond to 'a second processor'.

The Doppler-mode processor 5 extracts phase-change information from the echo signals received in the transmission and reception processor 2, and calculates flow information of, for example, the velocity, the dispersion, and the power wish respect to particular points of a cross-sectional surface of the target area substantially in real time for the user. Details of the Doppler-mode processor 5 will be described later.

The DSC 6 receives the B-mode image data from the B-mode processor 3 and/or the B-color-mode image data from the B-color-mode processor 4, and prepares B-mode images and/or B-color-mode images based on the received data. The DSC 6 also receives Doppler-mode images from the Doppler-mode processor 5. The DSC 6 then provides the display monitor 7 with the B-mode images and/or the B-color-mode images (hereinafter referred to as B-mode images unless otherwise stated) and the Doppler-mode images. The display monitor 7 displays the B-mode images and the Doppler-mode images.

The input unit 8 may include, for example, one or more of a keyboard, a trackball, a joystick, a mouse, a touch key panel, and a touch command screen. The input unit 8 is directly or indirectly coupled to the control unit 9. Through the input unit 8, the user may input several direct or indirect instructions including, but not limited to, for example, display style designation of the B-mode images and the Doppler-mode images and parameter designation of the Doppler segment period, the non-Doppler segment period, a scan-line density, the number of samples, an upper limit of a pulse repetition frequency, and a number of echo signals to receive in parallel, with respect to the B-mode scan. The scan-line density, the number of samples, the upper limit of the pulse repetition frequency, and the number of echo signals to receive in parallel may be hereinafter referred to as parameters. The number of samples means the number of ultrasound beam transmission and is hereinafter referred to as a sampling number. The input instructions are supplied to the control unit 9.

The input unit 8 may alternatively be connected to other device and work as an input interface so that instructions input in the connected device can be supplied to the control unit 9 through the input unit 8.

The control unit 9 may include a central processing unit (CPU) and a memory. The control unit 9 controls the transmission and reception processor 2 so as to control the transmission and the reception in the transmission and reception processor 2. The control unit 9 may also control the B-mode processor 3, the B-color-mode processor 4, and the Doppler-mode processor 4. The control unit 9 receives the instructions input through the input unit 8 and controls operations of the transmission and reception processor 2. the B-mode processor 3, the B-color-mode processor 4, and the Doppler-mode processor 5 based on the received instructions. For example, when the control unit 9 has received an instruction of the Doppler segment period, the control unit 9 sets the Doppler segment period in the transmission and reception processor 2. The transmission and reception processor 2 may correspond to 'a change unit'. Alternatively, the transmission and reception processor 2 and the control unit 9 may correspond to 'a change unit'. The control unit 9 may also correspond to 'a third processor'.

Figure 3:
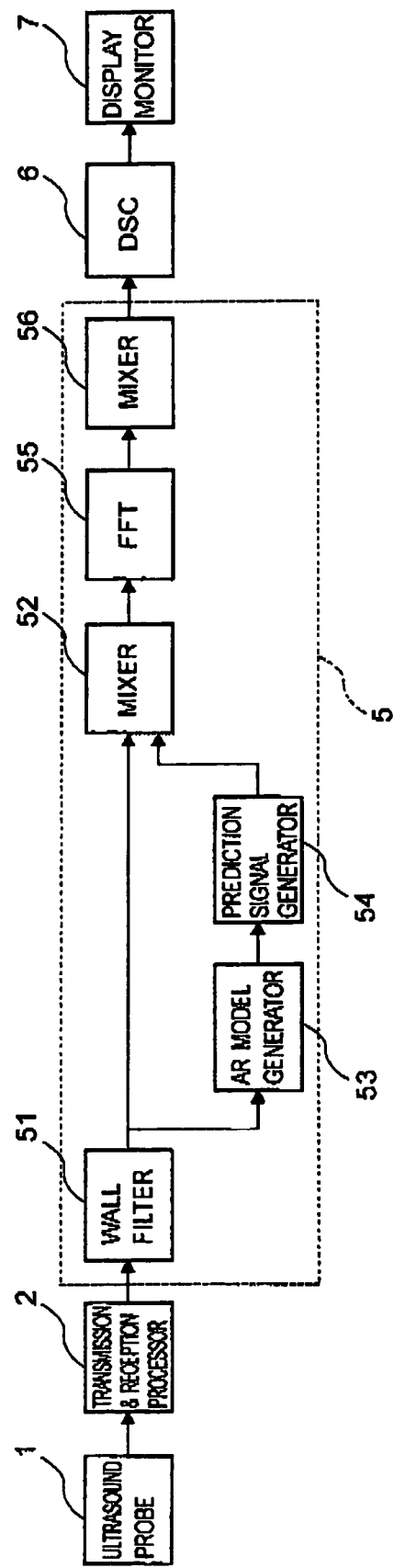
FIG. 3 is a block diagram showing an exemplary configuration of a Doppler-mode processor.

The Doppler-mode processor 5 will be described in detail with reference to FIG. 3. FIG. 3 is a block diagram showing an exemplary configuration of the Doppler-mode processor 5. The Doppler-mode processor 5 may include a wall filter 51, mixers 52 and 56, an AR model generator 53, a prediction signal generator 54, and a fast Fourier transformer (FFT) 55.

The echo signals received by the ultrasound probe 1 are quadrature-demodulated in the transmission and reception processor 2. Baseband Doppler signals obtained from the Quadrature demodulation are supplied to the wall filter 51. The wall filter 51 removes clutter components of the baseband Doppler signals. The Doppler signals from which the clutter components have been removed are supplied to the mixer 52 and the AR model generator 53.

The AR model generator 53 calculates linear predictive coefficients of AR models based on the Doppler signals supplied from the wall filter 51 in accordance with the Burg's maximum entropy method (MEN). The prediction signal generator 54 generates linearly predicted signals with respect to the non-Doppler segment period based on the linear predictive coefficients of AR models calculated in the AR model generator 53. The linearly predicted signals may be generated with Gaussian noise as a signal resource of the linearly predicted signals. The generated linearly predicted signals are supplied to the mixer 52 as signals to interpolate missing signals with respect to the non-Doppler segment period. The operations in the AR model generator 53 and the prediction signal generator 54 may be conducted during the non-Doppler segment period.

The mixer 52 mixes, that is, combines the Doppler signals supplied from the wall filter 51 and the linearly predicted signals supplied from the prediction signal generator 54. The combined signals are supplied to the FFT 55 as sequential Doppler signals.

The FFT 55 conducts frequency analyses on the supplied sequential Doppler signals and accordingly obtains a Doppler-mode image. The Doppler-mode image is supplied to the DSC 6 through the mixer 56. The DSC 6 synthesizes the Doppler-mode image with the prepared B-mode image. The synthesized Doppler-mode image and B-mode image are displayed in the display monitor 7. The AR model generator 53 and the prediction signal generator 54 may correspond to 'a predictionunit'. The mixer 52 and the FFT may correspond to 'a processor'.

In the above description, the Doppler signals supplied from the wall filter 51 and the linearly predicted signals supplied from the prediction signal generator 54 have been combined in the mixer 52 before the frequency analysis in the FFT 55, However, the Doppler signals and the linearly predicted signals may be combined after the frequency analysis.

According to the ultrasound diagnosis apparatus in the embodiments described above, the following operations may be realized.

When the user inputs instructions to designate the Doppler segment period, operating the input unit 8, signals corresponding to the designated Doppler segment period are provided to the control unit 9. The control unit 9 designates the Doppler segment period in the transmission and reception processor 2. The transmission and reception processor 2 changes the Doppler segment period based on the designation by the control unit 9. In other words, the transmission and reception processor 2 replaces the currently determined (or set) Doppler segment period with a new Doppler segment period which is designated by the Control unit 9. As a result, the ultrasound probe 1 transmits the ultrasound signals in the Doppler-mode during the newly determined Doppler segment period.

The control unit 9 also provides the Doppler-mode processor 5 with information of the Doppler segment period designated by the input unite 8. The Doppler-mode processor 5 conducts Doppler-mode processing in accordance with the designated Doppler segment period. Instead of instructing to change or designating the Doppler segment period, the user may instruct to change or designate the non-Doppler segment period. Further, the user may also instruct to change or designate both the Doppler segment period and the non-Doppler segment period.

Consequently, the B-mode image and the Doppler-mode image are available to the user according to the user's preference.

Figure 4A:
FIGS. 4A to 4C are illustrations for explaining various types of relationship between Doppler segment periods and non-Doppler segment periods.
Figure 4B:
Figure 4C:

Next, a relationship between the Doppler-mode image quality and the frame rate will be described with reference to FIGS. 4A to 4C. FIGS. 4A to 4C are illustrations for explaining various types of the relationship. In FIGS. 4A to 4C, 'B' represents the B-mode scan and 'D' represents the Doppler-mode scan.

As shown in FIG. 4A, the first example of the relationship pertains to a case that the non-Doppler segment period (i.e. B-mode scan period) is apparently shorter than the Doppler segment period (Doppler-mode scan period). Since the non-Doppler segment period is short, the Doppler-mode signal missing period is short, Therefore, it is not difficult to predict missing Doppler-mode signals for this period. Accordingly, the non-Doppler segment period may be well interpolated so that temporally-smooth Doppler-mode image is available. On the other hand, the B-mode scan is conducted only in three directions during each non-Doppler segment period, as shown in FIG. 4A. Therefore, it requires quite a large number of non-Doppler segment periods to complete one B-mode image. This leads to lowering the frame rate and providing B-mode images less in real time. In other words, it is difficult to display the B-mode images in real time.

The second example of the relationship pertains to a case that the non-Doppler segment period (i.e., B-mode scan period) is apparently longer than the Doppler segment period (Doppler-mode scan period), as shown in FIG. 4B. Since the non-Doppler segment period is long, the Doppler-mode signal missing period is long. Therefore, it is not easy to predict missing Doppler-mode signals for this period. Accordingly, the non-Doppler segment period may not be well interpolated so that temporally-unsmooth Doppler-mode image is available. In other words, vertically-striped spectrums may be displayed. On the other hand, the B-mode scan is conducted in nine directions during each non-Doppler segment period, as shown in FIG. 4B, therefore, it does not require a large number of non-Doppler segment periods to complete one B-mode image. This leads to a high frame rate and providing B-mode images better in real time. In other words, it is not difficult to display the B-mode images substantially in real time for the user.

The third example of the relationship pertains to a case that the non-Doppler segment period (i.e. B-mode scan period) is longer than one in the first example but shorter than one in the second example, as shown in FIG. 4C, Therefore, an available Doppler-mode image may be smoother than one available in the second example but not as smooth as one available in the first example. On the other hand, the frame rate of the B-mode image becomes higher than one in the first example but not as high as one in the second example.

In the ultrasound diagnosis apparatus, it is important to display ultrasound images substantially in real time for the user since such image display may make the user to more easily find lesion or disease. Therefore, it is optimally necessary to provide an ultrasound diagnosis apparatus which is operative at as high a frame rate as possible. The high frame rate makes it possible to present images substantially in real time for the user. As described before, when the Doppler segment period is apparently longer than the non-Doppler segment period, temporally-smooth Doppler-mode images are available while the B-mode images may neither become smooth nor be displayed in real time. Therefore, in order to display images substantially in real time for the user, the ultrasound diagnosis apparatus may further include features of decreasing the scan-line density, decreasing the sampling number, changing the upper limit of a pulse repetition frequency, and increasing the number of echo signals to receive in parallel, with respect to the B-mode scan. The ultrasound diagnosis apparatus may also include features of increasing the scan-line density, increasing the sampling number, and decreasing the number of echo signals to receive in parallel, with respect to the B-mode scan.

The user may instruct conditions of one or more of the parameters through the input unit B. The instructed conditions are provided to the control unit 9. The control unit 9 designates the instructed conditions in the transmission and reception processor 2. The transmission and reception processor 2 changes the Doppler segment period, the non-Doppler segment period, and/or the parameters as instructed, and then transmits ultrasound signals and receives echo signals under the changed conditions. The control unit 9 may also provide the instructed conditions to other processors. For example, if the instructed condition pertains to the scan-line density for the B-mode images, the control unit 9 provides the instructed condition to the B-mode processor 3, and the B-mode processor 3 prepares B-mode image data based on the B-mode scan conducted under the changed scan-line density. If the instructed condition pertains to the scan-line density for the B-color-mode images, the control-unit 9 provides the instructed condition to the B-color-mode processor 4, and the B-color-mode processor 4 prepares B-color-mode image data based on the B-color-mode scan conducted under the changed scan-line density.

For example, when the scan-line density is increased with respect to the B-mode scan, the B-mode image quality can be improved while the frame rate may be lowered. On the other hand, when the scan-line density is decreased with respect to the B-mode scan, the frame rate can be improved while the B-mode image quality may be deteriorated.

For example, when the sampling number is increased with respect to the B-color-mode scan the B-color-mode image quality can be improved while the frame rate may be lowered. On the other hand, when the sampling number is decreased with respect to the B-color-mode scan, the frame rate can be improved while the B-color-mode image quality may be deteriorated.

For example, when the number of echo signals to receive in parallel is increased with respect to the B-mode scan, echo signals returning from more number of directions can be received by the ultrasound probe 1 at the same time. Accordingly, the frame rate can be improved while the B-mode image quality may be deteriorated since the sensitivity and/or the spatial resolution may be lowered. On the other hand, when the number of echo signals to receive in parallel is decreased with respect to the B-mode scan, the B-mode image quality can be improved while the frame rate may be deteriorated.

The upper limit of a pulse repetition frequency may be changed as follows. If the ultrasound probe 1 transmits the ultrasound signals and receives the echo signals resulting from the transmitted ultrasound signals, residual echo signals may occur. When the echo signals cannot be received in the same predetermined period as the ultrasound transmission resulting in the echo signals and may be received in the next pulse repetition frequency period, such echo signals may be called the residual echo signals. To avoid the reception of the residual echo signals, the upper limit of the pulse repetition frequency may be changed so chat the echo signals can be received in the same predetermined period as the ultrasound transmission resulting in the echo signals. However, if the received echo signals are attenuated within a short period, it may waste time with respect to the reception time until the next ultrasound signals are generated. Therefore, the reception time may be effectively used by changing the upper limit of the pulse repetition frequency so as not to waste time. This may lead to the frame rate improvement.

Figure 5:
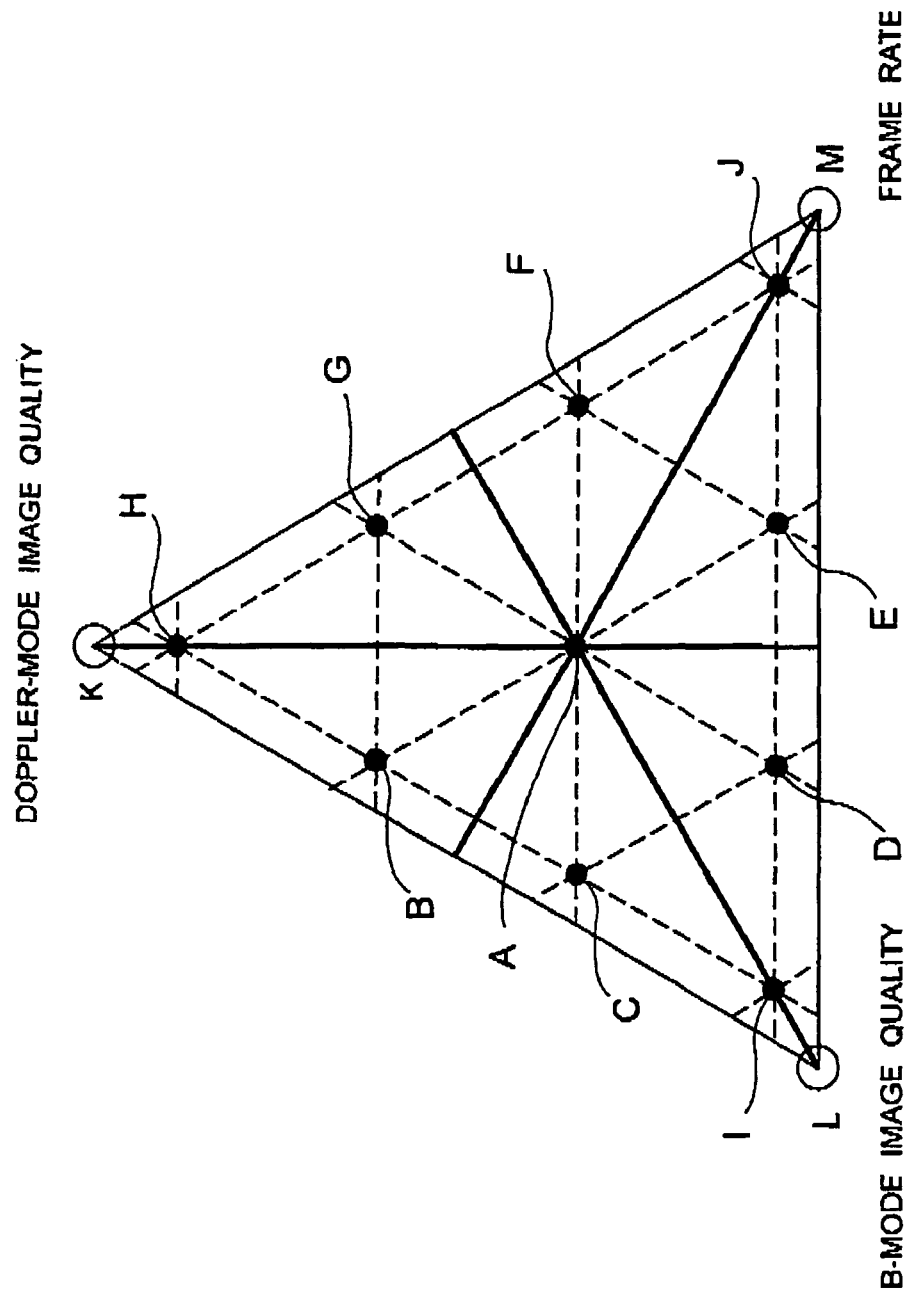
FIG. 5 is a chart of an example of a selectable condition map showing a relationship among an image quality of Doppler-mode image, an image quality of B-mode image, and a frame rate of B-mode scan.

As described above, the frame rate influencing a real time display and the B-mode image quality have a certain correlation. This correlation will be described with reference to FIG. 5. FIG. 5 is a chart of an example of a selectable condition map showing a relationship among the Doppler-mode image quality, the B-mode image quality, and the frame rate of V-mode scan. This selectable condition map shows not only the correlation between the frame race and the B-mode image quality, but also the correlation between the Doppler-mode image quality and the B-mode image quality and the correlation between the Doppler-mode image quality and the frame race.

In FIG. 5, regarding the Doppler-mode image, a point K represents the best Doppler-mode Image quality. Like points H and A, the further the point is from the point K, the more the quality of the Doppler-mode image becomes deteriorated. Regarding the B-mode image, a point L represents the best B-mode image quality. Like points I and A, the further the point is from the point L, the more the quality of the B-mode image becomes deteriorated. Regarding the frame rate, a point M represents the highest frame rate. Like points J and A, the further the point is from the point M, the lower the frame rate becomes. Further, for example, points B and G represent the same Doppler-mode image quality while points A, C, and F represent the same Doppler-mode image quality. Similarly, points D, E, I, J, L, and M represent the same Doppler-mode image quality.

The point A represents a well-balanced condition among the Doppler-mode image quality, the B-mode image quality, and the frame rate. At the point H, the Doppler-mode image quality is good, but the frame rate is low and the B-mode image quality is not good. At the point I, the B-mode image quality is good, but the frame rate is low and the Doppler-mode image quality is not good. At the point J, the frame rate is high, but the Doppler-mode image quality and the B-mode image quality are not good. Some users of an ultrasound diagnosis apparatus may prioritize the Doppler-mode image quality while some other users may prioritize the B-mode image quality. Or some other users may prioritize the frame rate so as to obtain an image display made substantially in real time. In addition, the preference may further depend on situations to observe images. According to this embodiment, the user may instruct to designate a desired condition among the Doppler-mode image quality, the B-mode image quality, and the frame rate.

For example, when the selectable condition map as shown in FIG. 5 is displayed in the display monitor 7, the user may operate the input unit 8 and designate desired one of the points A to M by bringing a cursor onto and clicking on the desired point.

The first example will be described, taking a case that the user designates the Point G. In this case, the user would like a frame rate at the same level as one available at the point A while the user prioritizes the Doppler-mode image quality, relative to the B-mode image quality. Responsive to the designation instruction, the control unit 9 controls the transmission and reception processor 2 to lengthen the Doppler segment period and make the non-Doppler segment period shorter than the Doppler segment period so that the Doppler-mode image quality can be improved. Also, the control unit 9 controls the transmission and reception processor 2 to decrease the scan line density and/or to Increase the number of echo signals to receive in parallel, with respect to the B-mode scan. In the event of the B-color-mode scan, the sampling number may be decreased. Accordingly, the frame rate can become reasonably high, Further, the control unit 9 may also control the transmission and reception processor 2 to change the upper limit of a pulse repetition frequency so Chat the reception time of the pulse repetition frequency cannot be wasted and can be used effectively. This change may also help to improve the frame rate. It may be noted that the above control may deteriorate the B-mode image quality.

The second example will be described, taking a case that the user designates the point C. In this case, the user would like the same Doppler-mode image quality as one available at the point A while the user prioritizes the B-mode image quality, relative to the Doppler-mode image quality. Responsive to the designation instruction, the control unit 9 controls the transmission and reception processor 2 to make the Doppler segment period and the non-Doppler segment period to be almost the same so that the Doppler-mode image quality can become almost the same asone available at the point A. Also, the control unit 9 controls the transmission and reception processor 2 to increase the scan-line density and/or to decrease the number of echo signals to receive in parallel, with respect to the B-mode scan. In the event of the B-color-mode scan, the sampling number may be increased. Accordingly, the B-mode image quality can be improved. It may be noted that the above control may lower the frame race.

The third example will be described, taking a case that the user designates the point F. In this case, the user would like the same Doppler-mode image quality as one available at the point A while the user prioritizes the frame rate. Responsive to the designation instruction, the control unit 9 controls the transmission and reception processor 2 to make the Doppler segment period and the non-Doppler segment period to be almost the same so that the Doppler-mode image quality can become almost the same as one available at the point A. Also, the control unit 9 controls the transmission and reception processor 2 to decrease the scan-line density and/or to increase the number of echo signals to receive in parallel, with respect to the B-mode scan. In the event of the B-color-mode scan, the sampling number may be decreased. Accordingly, the frame rate can become quite high. Further, the control unit 9 also controls the transmission and reception processor 2 to change the upper limit of a pulse repetition frequency so that the reception time of the pulse repetition frequency cannot be wasted and can be used effectively. This change may also help to improve the frame rate. It may be noted that the above control may deteriorate the B-mode image quality.

The fourth example will be described, taking a case that the user designates the point A. In this case, the user would like a balanced condition among the Doppler-mode image quality, the B-mode image quality, and the frame rate, Responsive to the designation instruction, the control unit 9 controls the transmission and reception processor 2 to make the Doppler segment period and the non-Doppler segment period to be almost the same so that both the Doppler-mode image quality and the B-mode image quality can become relatively good. Also, the control unit 9 controls the transmission and reception processor 2 to set the scan-line density and the number of echo signals to receive in parallel, with respect to the B-mode scan into a condition of between the condition determined at the point C and the condition determined at the point G. In the event of the B-color-mode scan, the sampling number may also be set in a condition between the points C and G. Accordingly, the balanced condition may be available.

The above examples at the points A, C, F, and G are only examples, and a similar condition change may be made in a manner appropriate for each of other points. Further, more number of points to be selected for the designation may be predetermined and provided in a similar selectable condition map. A selectable condition map showing points to be selected for the designation is not limited to the triangle shape as shown in FIG. 5, but any applicable shape or form may be used. Still further, the points may not necessarily be predetermined as shown in FIG. 5. For example, when a triangle figure is displayed in the display monitor 7 and its three apexes are assigned to the Doppler-mode image quality, the B-mode image quality, and the frame rate, respectively, the user may bring the cursor onto any point inside the triangle and click on the point. The control unit 9 may determine coordinates of the clicked-on point and control to change the conditions of one or more of the Doppler segment period, the non-Doppler segment period, and the parameters.

Figure 6:
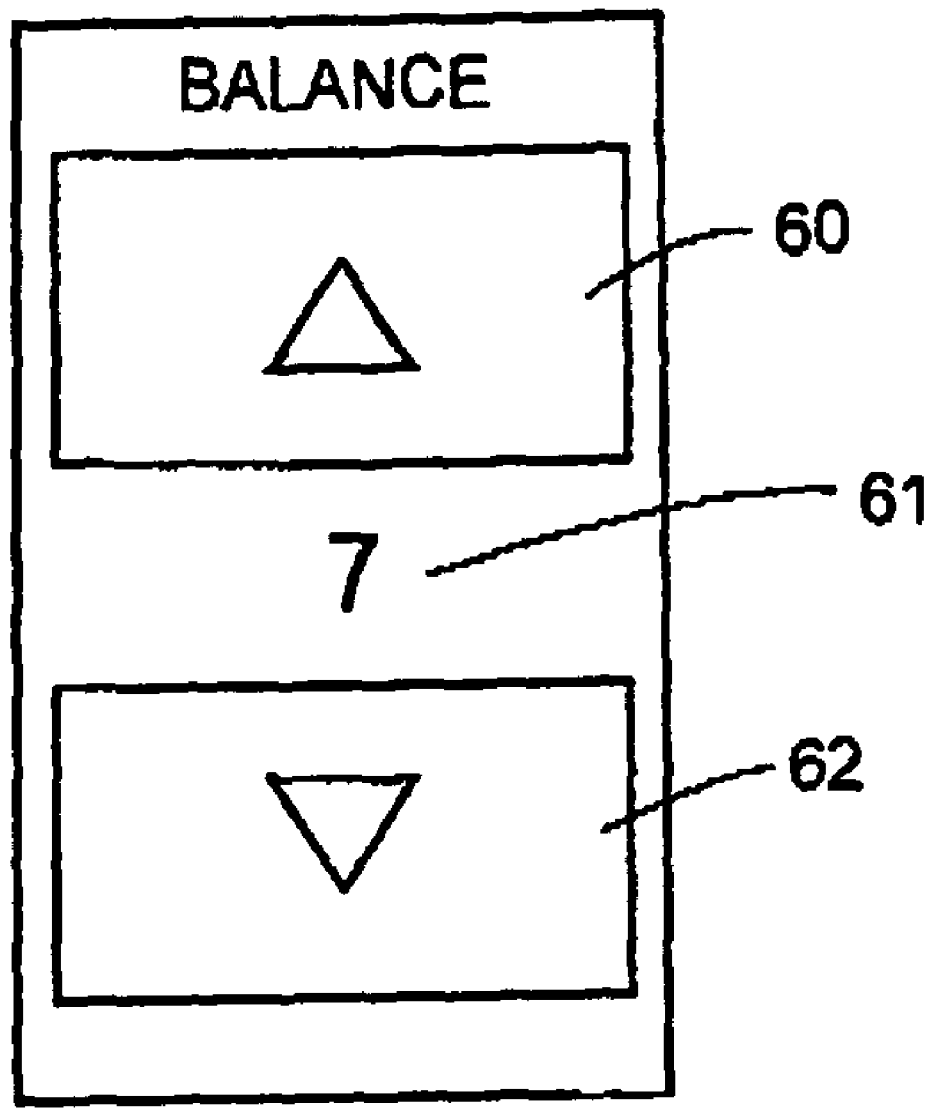
FIG. 6 is an illustration showing another example of an interface for instructing conditions.

Another example is shown in FIG. 6. FIG. 6 is an illustration showing another example of an interface for instructing similar conditions described above. The interface may be displayed in the display monitor 7. When the user brings the cursor onto and clicks on an increase-icon 60, a number shown in a numeric counter 61 increases. In FIG. 6, the numeric counter 61 shows '7' as an example of the number, similarly, when the user brings the cursor onto and clicks on a decrease-icon 62, the number shown in the numeric counter 61 decreases. The number may increase or decrease, for example, one by one in accordance with each one click-on. According to the number shown in the numeric counter 61, the control unit 9 may control to change the conditions of one or more of the Doppler segment period, the non-Doppler segment period, and the parameters. Alternatively, a similar interface may be provided for each of the Doppler segment period, the non-Doppler segment period, and the parameters.

In any above example, the user may not need to input specific conditions but can easily instruct desired conditions of the Doppler-mode image quality, the B-mode image quality, and the frame rate by selecting a predetermined point or predetermined selectable information. Any combination of the above examples may be applied to input instructions. After or without the instruction described above, the user may input specific numeric information of the above several conditions.

Instead of determining the conditions every time when the instruction is input, various sets of conditions of the Doppler segment period, the non-Doppler segment period, and the parameters may be predetermined and stored in the memory of the control unit 9 in correspondence with the selectable conditions. Accordingly, the control unit 9 may only need to extract a set of conditions stored in the memory in correspondence with a selectable condition (e.g., the point A in FIG. 5) instructed by the user through the input unit 8. The extracted set of conditions is provided to the transmission and reception processor 2. The transmission and reception processor 2 may be operative based on the provided conditions.

Figure 7A:
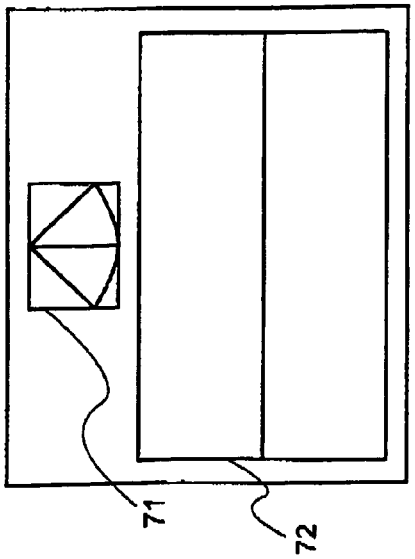
FIGS. 7A to 7D are illustrations showing display style examples of the Doppler-mode image and the B-mode image.
Figure 7B:
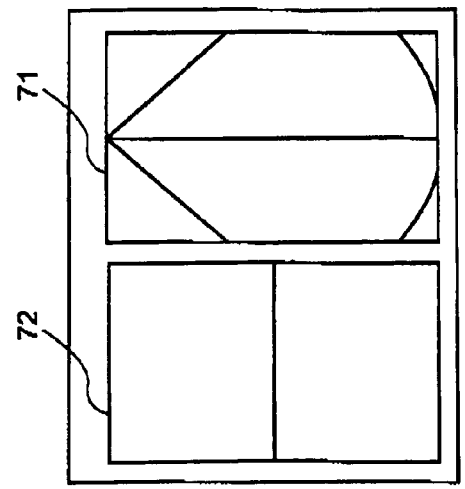
Figure 7C:
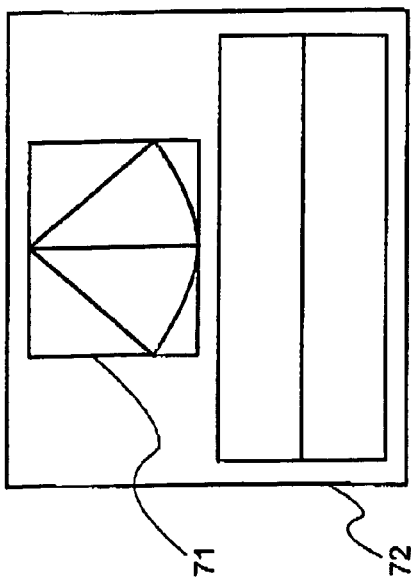
Figure 7D:
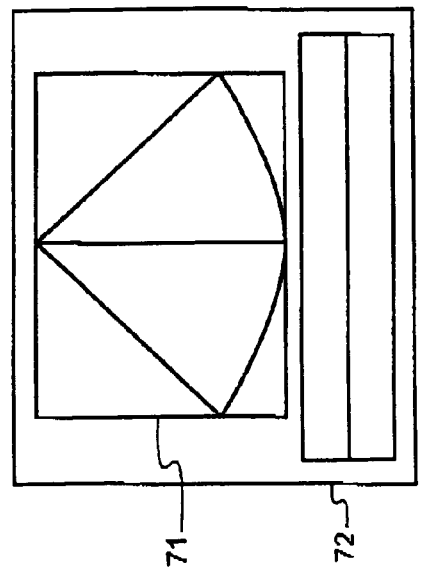

FIGS. 7A to 7D are illustrations showing display style examples of the Doppler-mode image and the B-mode image. In FIG. 7A, a B-mode image 71 and a Doppler-mode image 72 are displayed in a similar size. This display style may be advantageous when the user desires to equally observe the B-mode image 71 and the Doppler-mode image 72, In FIG. 7B, the Doppler-mode image 72 is displayed in a larger size than the B-mode image 71. This display style may be advantageous when the user desires to prioritize the Doppler-mode image 72 in the observation or to observe the Doppler-mode image 72 better than the B-mode image 71. In FIG. 7C, the B-mode image 71 is displayed in a larger size than the Doppler-mode image 72. This display style may be advantageous when the user desires to prioritize the B-mode image 71 in the observation or to observe the B-mode image 71 better than the Doppler-mode image 72. In FIG. 7D, the Doppler-mode image 72 and the B-mode image 71 are displayed side by side, and the B-mode image 71 may be displayed in its original size although the B-mode image 71 may only be displayed in part. This display style may be advantageous when the user desires to observe the B-mode image 71 in detail with reference to the Doppler-mode image 72.

These display styles may be stored, for example, in a memory of the display monitor 7. According to the user's preference, one of these display styles may be selected for example, by pressing one of buttons of the input unit 8 corresponding to the display styles or clicking on one of icons corresponding to the display styles. The selected display style information may be provided to the DSC 6 through the control unit 9. The DSC 6 may control the display monitor 7 to change its display style in accordance with the selected display style information.

Alternatively, an appropriate display style may be selected by the control unit 9 in accordance with the instructed and/or determined conditions of the Doppler segment period, the non-Doppler segment period, and the parameters. For example, when the Doppler segment period is instructed to become long so that the Doppler-mode image can be displayed in a good quality, the control unit 9 may select a display style shown in FIG. 7B. Accordingly, the Doppler-mode image and the B-mode image are displayed in the display style shown in FIG. 7B without the user's selection of any display style. For this operation, the control unit 9 may include a memory in which the display styles may be stored in correspondence or relation with display style determination references with respect to the conditions of the Doppler segment period, the non-Doppler segment period, and the parameters. When, for example, the control unit 9 receives an instruction to designate the Doppler segment period which is longer than a predetermined Doppler segment period reference (i.e. the display style determination reference), the control unit 9 determines the display style (e.g. FIG. 7B) stored in the memory in correspondence or relation with the predetermined Doppler segment period reference. Information of the determined display style may be provided to the DSC 6 from the control unit 9, The DSC 6 may control the display monitor 7 to change its display style in accordance with the determined display style.

Another alternative example is as follows. The conditions of one or more of the Doppler segment period, the non-Doppler segment period, and the parameters may be determined in accordance with a selected display style. One of the predetermined display styles may be selected according to the user's preference, as described above. The control unit 9 determines the conditions which are appropriate for the selected display style. The control unit 9 may alternatively select one of predetermined set of conditions which may be the most appropriate for the selected display style When the display style is changed by the selection, the conditions of one or more of the Doppler segment period, the non-Doppler segment period, and the parameters may be changed in accordance with the changed display style.

By correlating or associating the display styles with the conditions of the Doppler segment period, the non-Doppler segment period, and the parameters, it may be possible to display the Doppler-mode image and the B-mode image under preferable or desired display conditions.

In the above description, the Doppler segment period, the non-Doppler segment period, and the parameters have been described as the conditions to determine the Doppler-mode image quality, the B-mode image quality, and the frame rate. However, any other elements can be used as a part of the conditions for the purpose of determining the Doppler-mode image quality, the B-mode image quality, and the frame rate. The display styles to be selected are not limited to those shown in FIGS. 7A to 7D, but any other possible or preferable style may be used. One of the points A to M shown in FIG. 5 may be selected in accordance with inclining direction and degree of the joystick of the input unit 8.

In the above embodiments, the ultrasound diagnosis apparatus may have a random access memory (RAM), which can receive and store computer programs and applications as computer readable instructions in a temporary and/or non-volatile state. The ultrasound diagnosis apparatus may further have a hard disk drive as part of the control unit for reading from and writing to a hard disk, a magnetic disk drive for reading from and writing to a magnetic disk, and/or an optical disk drive for reading from and writing to an optical disk (such as a CD, CDR, CD-RW. DVD, or other optical device). Those skilled in the art will appreciate that one or more of such memory, drives, and their respective media are examples of a computer readable medium for storing computer readable instructions, which when executed, may implement an embodiment of the present invention.

The embodiments of the present invention described above are examples described only for making it easier to understand the present invention, and are nor described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

Numerous modifications and variations of the present invention are possible in light of the above teachings. It is therefore to be understood that within the scope of the appended claims, the invention may be practiced otherwise than as specifically described herein.

The invention claimed is:

1. An ultrasound diagnosis apparatus, comprising:
    a scanner configured to conduct an ultrasound segment scan by alternating a B-mode scan and a Doppler-mode scan;
    an input unit configured to receive, as input, an instruction;
    a display controller configured to cause a display unit to display a selectable condition map, wherein the instruction is a selection of one of predetermined points in the displayed selectable condition map; and
    a change unit configured to change a first period of the B-mode scan and a second period of the Doppler-mode scan in accordance with the instruction, the change unit further configured to change at least one of a scan-line density, a sampling number, an upper limit of a pulse repetition frequency, and a number of parallel receiving echo signals with respect to the B-mode scan, the echo signals resulting from ultrasound signals generated in the first period, in accordance with the received instruction.

2. The apparatus according to claim 1, wherein the display unit is configured to display at least one of the B-mode image and the Doppler-mode image in a predetermined style, wherein the predetermined style is changed in conjunction with the instruction for changing the first period of the B-mode scan and the second period of the Doppler-mode scan.

3. The apparatus according to claim 1, wherein the display unit is configured to display at least one of the B-mode image and the Doppler-mode image in a predetermined style, wherein at least one of the first period and the second period is changed in conjunction with the predetermined style, the echo signals resulting from ultrasound signals generated in the first period.

4. The apparatus according to claim 1, wherein the display unit displays the selectable condition map in which each of the predetermined points corresponds to a different set of parameters to determine an image quality of the B-mode image, an image quality of the Doppler-mode image, and a frame rate of the ultrasound segment scan, the parameters including the first period and the second period.

5. The apparatus according to claim 1, further comprising:
    a processor configured to calculate parameters to determine an image quality of the B-mode image, an image quality of the Doppler-mode image, and a frame rate of the ultrasound segment scan based on a point in the selectable condition map, the parameters including information of the first period and the second period.

6. The apparatus according to claim 1, wherein the instruction includes information to prioritize one of an image quality of the B-mode image, an image quality of the Doppler-mode image, and a frame rate of the ultrasound segment scan.

7. The apparatus according to claim 1, wherein the change unit is further configured to change the first period of the B-mode scan and the second period of the Doppler-mode scan in accordance with the instruction by designating a desired condition among Doppler image quality based on the Doppler-mode scan, B-mode image quality based on the B-mode scan, and a frame rate for the B-color mode scan.

8. A method of preparing a B-mode image and a Doppler-mode image using an ultrasound diagnosis apparatus, the method comprising:
    receiving an instruction into an input unit of the ultrasound diagnosis apparatus;
    displaying a selectable condition map, wherein the instruction is a selection of one of predetermined points in the selectable condition map; and
    changing at least one of a scan-line density, a sampling number, an upper limit of a pulse repetition frequency, and a number of echo signals to receive in parallel, with respect to the B-mode scan, the echo signals resulting from ultrasound signals generated in a first period in accordance with the instruction.

9. The method according to claim 8, further comprising displaying at least one of the B-mode image and the Doppler-mode image in a predetermined style, wherein the predetermined style is changed in conjunction with the instruction for changing the first period of the B-mode scan and the second period of the Doppler-mode scan.

10. The method according to claim 8, further comprising displaying at least one of the B-mode image and the Doppler-mode image in a predetermined style, wherein at least one of the first period and the second period is changed in conjunction with the predetermined style.

11. The method according to claim 8, wherein each of the predetermined points corresponds to a different set of parameters to determine an image quality of the B-mode image, an image quality of the Doppler-mode image, and a frame rate of the ultrasound segment scan, the parameters including the first period and the second period.

12. The method according to claim 8, further comprising calculating parameters to determine an image quality of the B-mode image, an image quality of the Doppler-mode image, and a frame rate of the ultrasound segment scan based on a point in the selectable condition map, the parameters including information of the first period and the second period.

13. The method according to claim 8, wherein the instruction includes information to prioritize one of an image quality of the B-mode image, an image quality of the Doppler-mode image, and a frame rate of the ultrasound segment scan.

14. The method of claim 8, wherein the displaying step comprises displaying the selectable condition map, wherein the selectable condition map includes the predetermined points that show a relationship among Doppler-mode image quality, B-mode image quality, and frame rate of the B-mode scan.

15. The method of claim 8, wherein the receiving step comprises selecting, by a user, one of the predetermined points in the selectable condition map, the selected point representing a preference of the user regarding a tradeoff among Doppler-mode image quality, B-mode image quality, and frame rate of the B-mode scan.

16. The method of claim 8, wherein the receiving step comprises selecting, by a user using a point device, one of the predetermined points in the selectable condition map.

* * * * *